(12) United States Patent
O'Neil et al.

(10) Patent No.: US 9,907,560 B2
(45) Date of Patent: Mar. 6, 2018

(54) FLEXIBLE VERTEBRAL BODY SHAVERS

(75) Inventors: Michael J. O'Neil, Raynham, MA (US); Douglas Raymond, Raynham, MA (US); John Riley Hawkins, Raynham, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 267 days.

(21) Appl. No.: 13/163,496

(22) Filed: Jun. 17, 2011

(65) Prior Publication Data

US 2011/0319899 A1  Dec. 29, 2011

Related U.S. Application Data

(60) Provisional application No. 61/379,194, filed on Sep. 1, 2010, provisional application No. 61/358,220, filed
(Continued)

(51) Int. Cl.
| | |
|---|---|
| A61B 17/16 | (2006.01) |
| A61F 2/44 | (2006.01) |
| A61B 17/17 | (2006.01) |
| A61M 29/02 | (2006.01) |
| A61F 2/46 | (2006.01) |
| A61B 5/00 | (2006.01) |
| A61B 17/02 | (2006.01) |
| A61B 17/34 | (2006.01) |
| A61M 25/00 | (2006.01) |
| A61M 25/01 | (2006.01) |

(52) U.S. Cl.
CPC ...... *A61B 17/1671* (2013.01); *A61B 17/1659* (2013.01); *A61B 17/1757* (2013.01); *A61F 2/446* (2013.01); *A61F 2/447* (2013.01); *A61F 2/4425* (2013.01); *A61F 2/4455* (2013.01); *A61F 2/4611* (2013.01); *A61M 29/02* (2013.01); *A61B 5/4893* (2013.01); *A61B 2017/0256* (2013.01); *A61B 2017/3433* (2013.01); *A61F 2/4465* (2013.01); *A61F 2002/443* (2013.01); *A61M 25/0054* (2013.01); *A61M 25/0133* (2013.01)

(58) Field of Classification Search
CPC .................................................. A61B 17/1671
USPC ........................................................... 606/84
See application file for complete search history.

(56) References Cited

U.S. PATENT DOCUMENTS

| 4,105,034 A | 8/1978 | Shalaby |
| 4,130,639 A | 12/1978 | Shalaby |

(Continued)

FOREIGN PATENT DOCUMENTS

| DE | 19710392 | 7/1999 |
| DE | 10357960 | 7/2005 |

(Continued)

OTHER PUBLICATIONS

US 5,545,827, 10/1995, Aust (withdrawn)
(Continued)

*Primary Examiner* — David Bates
*Assistant Examiner* — Olivia C Chang

(57) ABSTRACT

Several devices and methods for preparing the vertebral endplates while minimizing damage to the vertebral endplates. Each design incorporates flexible means to reduce endplate damage while enabling removal of the cartilage adhered to the endplate cortical bone.

3 Claims, 8 Drawing Sheets

Related U.S. Application Data on Jun. 24, 2010, provisional application No. 61/385,958, filed on Sep. 23, 2010, provisional application No. 61/410,177, filed on Nov. 4, 2010, provisional application No. 61/397,716, filed on Nov. 30, 2010, provisional application No. 61/466,302, filed on Mar. 22, 2011.

(56) References Cited

U.S. PATENT DOCUMENTS

| | | | |
|---|---|---|---|
| 4,140,678 A | 2/1979 | Shalaby | |
| 4,141,087 A | 2/1979 | Shalaby | |
| 4,205,399 A | 6/1980 | Shalaby | |
| 4,208,511 A | 6/1980 | Shalaby | |
| 4,538,612 A | 9/1985 | Patrick, Jr. | |
| 4,834,757 A | 5/1989 | Brantigan | |
| 4,863,476 A | 9/1989 | Shepperd | |
| 4,995,200 A * | 2/1991 | Eberhart | B24D 15/023 451/490 |
| 5,006,121 A | 4/1991 | Hafeli | |
| 5,019,082 A | 5/1991 | Frey | |
| 5,123,926 A | 6/1992 | Pisharodi | |
| 5,133,719 A | 7/1992 | Winston | |
| 5,163,939 A | 11/1992 | Winston | |
| 5,169,402 A | 12/1992 | Elloy | |
| 5,171,278 A | 12/1992 | Pisharodi | |
| 5,217,475 A | 6/1993 | Kuber | |
| 5,250,061 A | 10/1993 | Michelson | |
| 5,320,644 A | 6/1994 | Baumgartner | |
| 5,342,365 A | 8/1994 | Waldman | |
| 5,387,215 A | 2/1995 | Fisher | |
| 5,390,683 A | 2/1995 | Pisharodi | |
| 5,454,815 A | 10/1995 | Geisser | |
| 5,454,827 A | 10/1995 | Aust | |
| 5,464,929 A | 11/1995 | Bezwada | |
| 5,522,899 A | 6/1996 | Michelson | |
| 5,540,693 A | 7/1996 | Fisher | |
| 5,554,191 A * | 9/1996 | Lahille | A61B 17/1757 411/55 |
| 5,595,751 A | 1/1997 | Bezwada | |
| 5,597,579 A | 1/1997 | Bezwada | |
| 5,601,561 A | 2/1997 | Terry | |
| 5,607,687 A | 3/1997 | Bezwada | |
| 5,618,552 A | 4/1997 | Bezwada | |
| 5,620,698 A | 4/1997 | Bezwada | |
| 5,645,850 A | 7/1997 | Bezwada | |
| 5,648,088 A | 7/1997 | Bezwada | |
| 5,658,335 A | 8/1997 | Allen | |
| 5,665,122 A | 9/1997 | Kambin | |
| 5,693,100 A | 12/1997 | Pisharodi | |
| 5,698,213 A | 12/1997 | Jamiolkowski | |
| 5,700,583 A | 12/1997 | Jamiolkowski | |
| 5,725,531 A | 3/1998 | Shapiro | |
| 5,857,995 A | 1/1999 | Thomas | |
| 5,859,150 A | 1/1999 | Jamiolkowski | |
| 5,865,848 A | 2/1999 | Baker | |
| 5,916,228 A | 6/1999 | Ripich | |
| 5,925,056 A | 7/1999 | Thomas | |
| 5,976,187 A | 11/1999 | Richelsoph | |
| 5,980,522 A | 11/1999 | Koros | |
| 6,039,761 A | 3/2000 | Li | |
| 6,045,579 A | 4/2000 | Hochshuler et al. | |
| 6,053,922 A | 4/2000 | Krause | |
| 6,056,763 A | 5/2000 | Parsons | |
| 6,066,175 A | 5/2000 | Henderson | |
| 6,080,158 A | 6/2000 | Lin | |
| 6,106,557 A | 8/2000 | Robioneck | |
| 6,120,508 A | 9/2000 | Grunig | |
| 6,126,689 A | 10/2000 | Brett | |
| 6,139,558 A | 10/2000 | Wagner | |
| 6,176,882 B1 | 1/2001 | Biedermann | |
| 6,241,733 B1 * | 6/2001 | Nicholson et al. | 606/84 |
| 6,251,140 B1 | 6/2001 | Marino | |
| 6,258,093 B1 | 7/2001 | Edwards | |
| 6,296,644 B1 | 10/2001 | Saurat | |
| D450,676 S | 11/2001 | Huttner | |
| 6,332,894 B1 | 12/2001 | Stalcup et al. | |
| 6,342,074 B1 | 1/2002 | Simpson | |
| 6,387,130 B1 | 5/2002 | Stone | |
| 6,398,793 B1 | 6/2002 | McGuire | |
| 6,409,766 B1 | 6/2002 | Brett | |
| 6,413,278 B1 | 7/2002 | Marchosky | |
| 6,436,101 B1 | 8/2002 | Hamada | |
| 6,447,518 B1 | 9/2002 | Krause | |
| 6,595,998 B2 | 7/2003 | Johnson et al. | |
| 6,610,066 B2 | 8/2003 | Dinger | |
| 6,635,060 B2 | 10/2003 | Hanson | |
| RE38,335 E | 11/2003 | Aust | |
| 6,641,582 B1 | 11/2003 | Hanson | |
| 6,660,004 B2 | 12/2003 | Barker | |
| 6,733,535 B2 | 5/2004 | Michelson | |
| 6,755,837 B2 | 6/2004 | Ebner | |
| 6,764,491 B2 | 7/2004 | Frey | |
| 6,835,208 B2 | 12/2004 | Marchosky | |
| 6,840,941 B2 | 1/2005 | Rogers | |
| 6,878,167 B2 | 4/2005 | Ferree | |
| 6,949,108 B2 | 9/2005 | Holmes | |
| 6,966,912 B2 | 11/2005 | Michelson | |
| 7,018,415 B1 | 3/2006 | McKay | |
| 7,060,073 B2 | 6/2006 | Frey | |
| 7,070,598 B2 | 7/2006 | Lim | |
| 7,087,055 B2 | 8/2006 | Lim | |
| 7,125,424 B2 | 10/2006 | Banick | |
| 7,226,482 B2 | 6/2007 | Messerli | |
| 7,326,248 B2 | 2/2008 | Michelson | |
| 7,351,262 B2 | 4/2008 | Bindseil | |
| 7,470,273 B2 | 12/2008 | Dougherty-Shah | |
| 7,491,237 B2 | 2/2009 | Randall | |
| 7,503,920 B2 | 3/2009 | Siegal | |
| 7,572,279 B2 | 8/2009 | Jackson | |
| 7,575,580 B2 | 8/2009 | Lim | |
| 7,578,820 B2 | 8/2009 | Moore | |
| 7,601,173 B2 | 10/2009 | Messerli | |
| 7,618,458 B2 | 11/2009 | Biedermann | |
| 7,625,377 B2 | 12/2009 | Veldhuizen | |
| 7,625,394 B2 | 12/2009 | Molz, IV | |
| 7,655,010 B2 | 2/2010 | Serhan et al. | |
| 7,666,186 B2 | 2/2010 | Harp | |
| 7,666,226 B2 | 2/2010 | Schaller | |
| 7,670,374 B2 | 3/2010 | Schaller | |
| 7,674,265 B2 | 3/2010 | Smith | |
| 7,682,400 B2 | 3/2010 | Zwirkoski | |
| 7,703,727 B2 | 4/2010 | Selness | |
| 7,704,280 B2 | 4/2010 | Lechmann | |
| 7,731,751 B2 | 6/2010 | Butler | |
| 7,763,028 B2 | 7/2010 | Lim | |
| 7,771,473 B2 | 8/2010 | Thramann | |
| 7,785,368 B2 | 8/2010 | Schaller | |
| 7,799,081 B2 | 9/2010 | McKinley | |
| 7,803,161 B2 | 9/2010 | Foley | |
| 7,828,849 B2 | 11/2010 | Lim | |
| 7,837,734 B2 | 11/2010 | Zucherman | |
| 7,850,733 B2 | 12/2010 | Baynham | |
| 7,918,874 B2 | 4/2011 | Siegal | |
| 7,922,719 B2 | 4/2011 | Ralph | |
| 7,938,857 B2 | 5/2011 | Garcia-Bengochea | |
| 7,942,903 B2 | 5/2011 | Moskowitz | |
| 7,963,967 B1 | 6/2011 | Woods | |
| 8,007,535 B2 | 8/2011 | Hudgins | |
| 8,012,212 B2 | 9/2011 | Link | |
| 8,025,697 B2 | 9/2011 | McClellan, III | |
| 8,034,110 B2 | 10/2011 | Garner et al. | |
| 8,038,703 B2 | 10/2011 | Dobak, III | |
| 8,043,293 B2 | 10/2011 | Warnick | |
| 8,057,544 B2 | 11/2011 | Schaller | |
| 8,105,382 B2 | 1/2012 | Olmos | |
| 8,128,700 B2 | 3/2012 | Delurio | |
| 8,206,423 B2 | 6/2012 | Siegal | |
| 8,216,317 B2 | 7/2012 | Thibodeau | |
| 8,241,364 B2 | 8/2012 | Hansell | |
| 8,262,666 B2 | 9/2012 | Baynham | |
| 8,267,939 B2 | 9/2012 | Cipoletti | |
| 8,343,193 B2 | 1/2013 | Johnson et al. | |
| 8,343,222 B2 | 1/2013 | Cope | |

(56) References Cited

U.S. PATENT DOCUMENTS

| | | |
|---|---|---|
| 8,366,777 B2 | 2/2013 | Matthis |
| 8,382,842 B2 | 2/2013 | Greenhalgh et al. |
| 8,403,990 B2 | 3/2013 | Dryer et al. |
| 8,454,617 B2 | 6/2013 | Schaller et al. |
| 8,579,981 B2 | 11/2013 | Lim |
| 8,628,577 B1 | 1/2014 | Jimenez |
| 8,663,331 B2 | 3/2014 | McClellan, III |
| 8,845,733 B2 | 9/2014 | O'Neil |
| 8,845,734 B2 | 9/2014 | Weiman |
| 8,920,506 B2 | 12/2014 | McGuckin, Jr. |
| 8,926,704 B2 | 1/2015 | Glerum et al. |
| 8,940,050 B2 | 1/2015 | Laurence |
| 8,961,609 B2 | 2/2015 | Schaller |
| 8,968,408 B2 | 3/2015 | Schaller et al. |
| 9,101,488 B2 | 8/2015 | Malandain |
| 9,101,492 B2 | 8/2015 | Mangione |
| 2002/0138078 A1 | 9/2002 | Chappuis |
| 2002/0143399 A1 | 10/2002 | Sutcliffe |
| 2002/0165550 A1 | 11/2002 | Frey |
| 2002/0183758 A1 | 12/2002 | Middleton |
| 2003/0028251 A1 | 2/2003 | Matthews |
| 2003/0135275 A1 | 7/2003 | Garcia |
| 2003/0139812 A1 | 7/2003 | Garcia et al. |
| 2003/0191531 A1 | 10/2003 | Berry |
| 2004/0002761 A1 | 1/2004 | Rogers et al. |
| 2004/0030387 A1 | 2/2004 | Landry |
| 2004/0059337 A1 | 3/2004 | Hanson |
| 2004/0068269 A1 | 4/2004 | Bonati |
| 2004/0083000 A1 | 4/2004 | Keller |
| 2004/0087947 A1 | 5/2004 | Lim et al. |
| 2004/0102784 A1 | 5/2004 | Pasquet |
| 2004/0102846 A1 | 5/2004 | Keller |
| 2004/0127990 A1 | 7/2004 | Bartish |
| 2004/0147129 A1 | 7/2004 | Rolfson |
| 2004/0220668 A1 | 11/2004 | Eisermann |
| 2005/0038431 A1 | 2/2005 | Bartish |
| 2005/0096745 A1 | 5/2005 | Andre |
| 2005/0119752 A1 | 6/2005 | Williams et al. |
| 2005/0149034 A1 | 7/2005 | Assell |
| 2005/0165420 A1 | 7/2005 | Cha |
| 2005/0165484 A1 | 7/2005 | Ferree |
| 2005/0171541 A1 | 8/2005 | Boehm |
| 2005/0177173 A1 | 8/2005 | Aebi |
| 2005/0240193 A1 | 10/2005 | Layne |
| 2006/0036244 A1 | 2/2006 | Spitler |
| 2006/0058807 A1 | 3/2006 | Landry |
| 2006/0064101 A1 | 3/2006 | Arramon |
| 2006/0064102 A1 | 3/2006 | Ebner |
| 2006/0069436 A1 | 3/2006 | Sutton |
| 2006/0074429 A1 | 4/2006 | Ralph |
| 2006/0100622 A1 | 5/2006 | Jackson |
| 2006/0111715 A1 | 5/2006 | Jackson |
| 2006/0111728 A1 | 5/2006 | Abdou |
| 2006/0122701 A1 | 6/2006 | Kiester |
| 2006/0129244 A1 | 6/2006 | Ensign |
| 2006/0142858 A1 | 6/2006 | Colleran |
| 2006/0167547 A1 | 7/2006 | Suddaby |
| 2006/0189999 A1 | 8/2006 | Zwirkoski |
| 2006/0212118 A1 | 9/2006 | Abernathie |
| 2006/0229627 A1 | 10/2006 | Hunt |
| 2006/0235426 A1 | 10/2006 | Lim |
| 2006/0253120 A1 | 11/2006 | Anderson |
| 2006/0254784 A1 | 11/2006 | Hartmann |
| 2006/0265077 A1 | 11/2006 | Zwirkoski |
| 2006/0293753 A1 | 12/2006 | Thramann |
| 2007/0055264 A1 | 3/2007 | Parmigiani |
| 2007/0055272 A1 | 3/2007 | Schaller |
| 2007/0067035 A1 | 3/2007 | Falahee |
| 2007/0093897 A1 | 4/2007 | Gerbec |
| 2007/0093901 A1 | 4/2007 | Grotz et al. |
| 2007/0142843 A1 | 6/2007 | Dye |
| 2007/0162132 A1 | 7/2007 | Messerli |
| 2007/0213737 A1 | 9/2007 | Schermerhorn |
| 2007/0213826 A1 | 9/2007 | Smith |
| 2007/0225726 A1 | 9/2007 | Dye |
| 2007/0225815 A1 | 9/2007 | Keith |
| 2007/0233130 A1 | 10/2007 | Suddaby |
| 2007/0250167 A1 | 10/2007 | Bray et al. |
| 2007/0260314 A1 | 11/2007 | Biyani |
| 2007/0270957 A1 | 11/2007 | Heinz |
| 2007/0270968 A1 | 11/2007 | Baynham |
| 2008/0027544 A1 | 1/2008 | Melkent |
| 2008/0027550 A1 | 1/2008 | Link |
| 2008/0045966 A1 | 2/2008 | Buttermann |
| 2008/0051890 A1 | 2/2008 | Waugh |
| 2008/0058933 A1 | 3/2008 | Garner |
| 2008/0065082 A1 | 3/2008 | Chang |
| 2008/0077150 A1 | 3/2008 | Nguyen |
| 2008/0077241 A1 | 3/2008 | Nguyen |
| 2008/0082173 A1 | 4/2008 | Delurio |
| 2008/0091211 A1 | 4/2008 | Gately |
| 2008/0097454 A1 | 4/2008 | DeRidder |
| 2008/0108990 A1 | 5/2008 | Mitchell |
| 2008/0119935 A1 | 5/2008 | Alvarez |
| 2008/0125865 A1 | 5/2008 | Abdelgany |
| 2008/0133012 A1 | 6/2008 | McGuckin |
| 2008/0140085 A1 | 6/2008 | Gately |
| 2008/0154379 A1 | 6/2008 | Steiner |
| 2008/0172128 A1 | 7/2008 | Perez-Cruet et al. |
| 2008/0208255 A1 | 8/2008 | Siegal |
| 2008/0221586 A1 | 9/2008 | Garcia-Bengochea |
| 2008/0221687 A1 | 9/2008 | Viker |
| 2008/0234732 A1 | 9/2008 | Landry |
| 2008/0234733 A1 | 9/2008 | Scrantz |
| 2008/0243126 A1 | 10/2008 | Gutierrez |
| 2008/0243255 A1 | 10/2008 | Butler |
| 2008/0249628 A1 | 10/2008 | Altarac |
| 2008/0255563 A1 | 10/2008 | Farr |
| 2008/0255574 A1 | 10/2008 | Dye |
| 2008/0269904 A1 | 10/2008 | Voorhies |
| 2008/0312743 A1 | 12/2008 | Vila |
| 2009/0030423 A1 | 1/2009 | Puno |
| 2009/0054898 A1 | 2/2009 | Gleason |
| 2009/0054911 A1 | 2/2009 | Mueller |
| 2009/0062807 A1 | 3/2009 | Song |
| 2009/0076607 A1 | 3/2009 | Aalsma |
| 2009/0088789 A1 | 4/2009 | O'Neil |
| 2009/0112217 A1 | 4/2009 | Hester |
| 2009/0143859 A1 | 6/2009 | McClellan, III |
| 2009/0182431 A1 | 7/2009 | Butler |
| 2009/0192616 A1 | 7/2009 | Zielinski |
| 2009/0216234 A1 | 8/2009 | Farr |
| 2009/0234364 A1 | 9/2009 | Crook |
| 2009/0240335 A1 | 9/2009 | Arcenio |
| 2009/0276049 A1 | 11/2009 | Weiland |
| 2009/0299479 A1 | 12/2009 | Jones |
| 2010/0016968 A1 | 1/2010 | Moore |
| 2010/0030217 A1 | 2/2010 | Mitusina |
| 2010/0076502 A1 | 3/2010 | Guyer |
| 2010/0094422 A1 | 4/2010 | Hansell |
| 2010/0100098 A1 | 4/2010 | Norton |
| 2010/0125334 A1 | 5/2010 | Krueger |
| 2010/0161060 A1 | 6/2010 | Schaller |
| 2010/0174321 A1 | 7/2010 | Schaller |
| 2010/0185290 A1 | 7/2010 | Compton |
| 2010/0191241 A1* | 7/2010 | McCormack et al. .......... 606/83 |
| 2010/0198263 A1 | 8/2010 | Siegal |
| 2010/0211076 A1 | 8/2010 | Germain |
| 2010/0211107 A1 | 8/2010 | Muhanna |
| 2010/0217269 A1 | 8/2010 | Landes |
| 2010/0234849 A1 | 9/2010 | Bouadi |
| 2010/0249935 A1 | 9/2010 | Slivka |
| 2010/0256768 A1 | 10/2010 | Lim |
| 2010/0274358 A1 | 10/2010 | Mueller et al. |
| 2010/0280619 A1 | 11/2010 | Yuan |
| 2010/0305700 A1 | 12/2010 | Ben-Arye |
| 2010/0305704 A1 | 12/2010 | Messerli |
| 2010/0331845 A1 | 12/2010 | Foley |
| 2011/0004216 A1 | 1/2011 | Amendola |
| 2011/0009970 A1 | 1/2011 | Puno |
| 2011/0029083 A1 | 2/2011 | Hynes |
| 2011/0029085 A1 | 2/2011 | Hynes |
| 2011/0035011 A1 | 2/2011 | Cain |
| 2011/0106260 A1 | 5/2011 | Laurence |

(56) References Cited

U.S. PATENT DOCUMENTS

| | | |
|---|---|---|
| 2011/0112586 A1 | 5/2011 | Guyer |
| 2011/0125266 A1 | 5/2011 | Rodgers |
| 2011/0190891 A1 | 8/2011 | Suh et al. |
| 2011/0276142 A1 | 11/2011 | Niemiec |
| 2011/0282459 A1 | 11/2011 | McClellan, III |
| 2011/0301712 A1 | 12/2011 | Palmatier et al. |
| 2011/0319898 A1 | 12/2011 | O'Neil |
| 2011/0319899 A1 | 12/2011 | O'Neil |
| 2011/0319998 A1 | 12/2011 | O'Neil |
| 2011/0319999 A1 | 12/2011 | O'Neil |
| 2011/0320000 A1 | 12/2011 | O'Neil |
| 2012/0035730 A1 | 2/2012 | Spann |
| 2012/0165943 A1 | 6/2012 | Mangione |
| 2012/0209383 A1 | 8/2012 | Tsuang |
| 2012/0277877 A1 | 11/2012 | Smith |
| 2012/0310352 A1 | 12/2012 | DiMauro et al. |
| 2013/0006362 A1 | 1/2013 | Biedermann |
| 2013/0023937 A1 | 1/2013 | Biedermann |
| 2013/0035762 A1 | 2/2013 | Siegal |
| 2013/0079790 A1 | 3/2013 | Stein |
| 2013/0109925 A1 | 5/2013 | Horton |
| 2013/0110239 A1 | 5/2013 | Siegal et al. |
| 2013/0116791 A1 | 5/2013 | Theofilos |
| 2013/0138214 A1 | 5/2013 | Greenhalgh |
| 2013/0150906 A1 | 6/2013 | Kerboul |
| 2013/0173004 A1 | 7/2013 | Greenhalgh |
| 2013/0190875 A1 | 7/2013 | Shulock |
| 2013/0238006 A1 | 9/2013 | O'Neil |
| 2013/0268077 A1 | 10/2013 | You |
| 2013/0310937 A1 | 11/2013 | Pimenta |
| 2014/0025170 A1 | 1/2014 | Lim |
| 2014/0039626 A1 | 2/2014 | Mitchell |
| 2014/0052259 A1 | 2/2014 | Garner et al. |
| 2014/0058512 A1 | 2/2014 | Petersheim |
| 2014/0058513 A1 | 2/2014 | Gahman |
| 2014/0172103 A1 | 6/2014 | O'Neil |
| 2014/0172105 A1 | 6/2014 | Frasier |
| 2015/0032212 A1 | 1/2015 | O'Neil |
| 2015/0094812 A1 | 4/2015 | Cain |
| 2015/0196400 A1 | 7/2015 | Dace |
| 2016/0038306 A1 | 2/2016 | Oneil |
| 2017/0128231 A1 | 5/2017 | O'Neil |

FOREIGN PATENT DOCUMENTS

| | | |
|---|---|---|
| EP | 609084 | 9/1997 |
| EP | 1283026 | 9/2003 |
| EP | 1405602 | 4/2004 |
| EP | 1605836 | 12/2005 |
| EP | 1308132 | 12/2006 |
| EP | 1829486 | 9/2007 |
| FR | 2874814 | 3/2006 |
| FR | 2948277 | 1/2011 |
| WO | WO 9214423 | 9/1992 |
| WO | WO 9834568 | 8/1998 |
| WO | WO 9960956 | 12/1999 |
| WO | WO 9963914 | 12/1999 |
| WO | WO 0024343 | 5/2000 |
| WO | WO 0074605 | 12/2000 |
| WO | WO 0203870 | 1/2002 |
| WO | WO 03003951 | 1/2003 |
| WO | WO 2004069033 | 8/2004 |
| WO | WO 2004080316 | 9/2004 |
| WO | WO 2005094297 | 10/2005 |
| WO | WO 2006044920 | 4/2006 |
| WO | WO 2006072941 | 7/2006 |
| WO | WO 2006118944 | 11/2006 |
| WO | WO 2007048012 | 4/2007 |
| WO | WO 2008005627 | 1/2008 |
| WO | WO 2010011348 | 1/2010 |
| WO | WO 2010075555 | 10/2010 |
| WO | WO 2010121002 | 12/2010 |
| WO | WO 2011013047 | 4/2011 |
| WO | WO 2011060087 | 5/2011 |
| WO | WO 2012027490 | 3/2012 |
| WO | WO 2012103254 | 8/2012 |
| WO | WO 2012129197 | 9/2012 |
| WO | WO 2013149611 | 10/2013 |

OTHER PUBLICATIONS

U.S. Appl. No. 61/140,926.
U.S. Appl. No. 61/178,315.
Vandorpe, "Biodegradable Polyphosphazenes for Biomedical Applications"; *Handbook of Biodegradable Polymers*; 1997; pp. 161-182; Hardwood Academic Press.
Allcock, "Polyphosphazenes"; *The Encyclopedia of Polymer Science*; 1988; pp. 31-41; vol. 13; Wiley Intersciences, John Wiley & Sons.
Cohn, "Polymer Preprints"; *Journal of Biomaterials Research*; 1989; p. 498; Biomaterials Research Labortatory, Casali Institute of Applied Chemistry, Israel.
Cohn, "Biodegradable PEO/PLA Block Copolymers"; *Journal of Biomedical Materials Research*; 1988; pp. 993-1009; vol. 22; John Wiley & Sons, Inc.
Heller, "Poly (Otrho Esters)"; *Handbook of Biodegradable Polymers*; edited by Domb; et al; Hardwood Academic Press; 1997; pp. 99-118.
Kemnitzer, "Degradable Polymers Derived From the Amino Acid L-Tyrosine"; 1997; pp. 251-272; edited by Domb, et. al., Hardwood Academic Press.
Khoo, Axilif address spongy from the caudal approach. Minimally Invasive Correction of Grage I and II Isthmic Spondylolisthesis using AsiaLiF for L5/S1 Fusion, pp. 45-0123 Rev B Sep. 15, 2008.
U.S. Appl. No. 61/009,546, filed Dec. 28, 2007 Rodgers.
U.S. Appl. No. 61/140,926, filed Dec. 26, 2008 Spann.
U.S. Appl. No. 61/178,315, filed May 14, 2009 Spann.

* cited by examiner

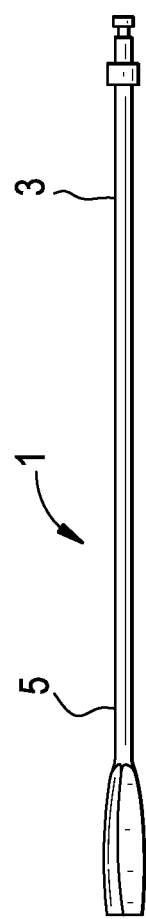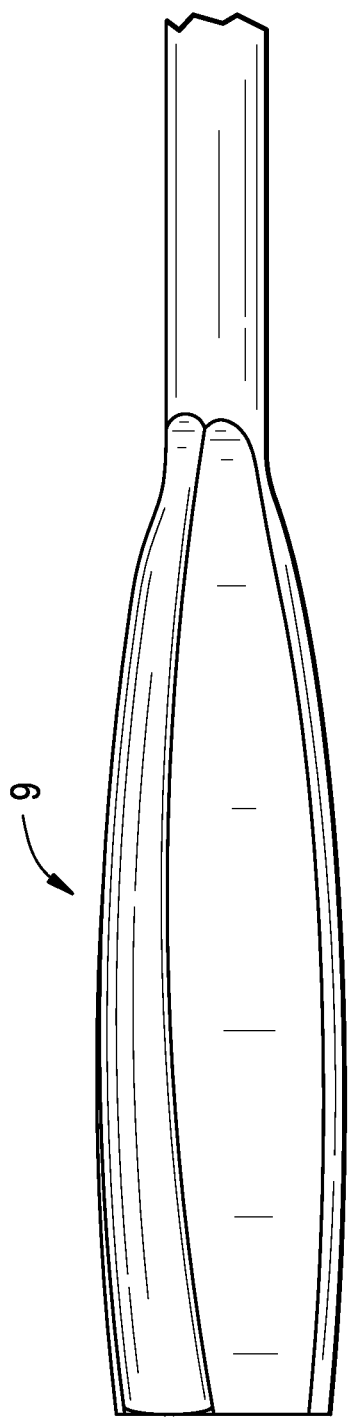

FLEXIBLE VERTEBRAL BODY SHAVERS

RELATED APPLICATIONS

This application claims priority from provisional application U.S. Ser. No. 61/379,194, filed Sep. 1, 2010, entitled Flexible Vertebral Body Shavers, the specification of which is incorporated by reference in its entirety This application claims priority from provisional application U.S. Ser. No. 61/358220, filed Jun. 24, 2010, entitled Instruments and Methods for Non-Parallel Disc Space Preparation, and is related to non-provisional U.S. Ser. No. 13/163,471, filed on Jun. 17, 2011 which has granted as U.S. Pat. No. 9,282,979 entitled Instruments and Methods for Non-Parallel Disc Space Preparation, the specifications of which are incorporated by reference in their entireties.

This application claims priority from provisional application U.S. Ser. No. 61/385,958, filed Sept. 23, 2010, and entitled "Multi-Segment Lateral Cages adapted to Flex Substantially in the Coronal Plane", the specification of which is incorporated by reference in its entirety.

This application claims priority from provisional application U.S. Ser. No. 61/410,177, filed Nov. 4, 2010, and entitled "Multi-Segment Lateral Cages adapted to Flex Substantially in the Coronal Plane", the specification of which is incorporated by reference in its entirety.

This application is related to non-provisional U.S. Ser. No. 13/163,517, filed on, Jun. 17, 2011, entitled "Multi-Segment Lateral Cages adapted to Flex Substantially in the Coronal Plane", the specification of which is incorporated by reference in its entirety.

This application claims priority from provisional application U.S. Ser. No. 61/397,716, filed Nov. 30, 2010, and entitled "Lateral Spondylolisthesis Reduction Cage", and is related to non-provisional U.S. Ser. No. 12/956,337, filed on Jun. 17, 2011, entitled "Lateral Spondylolisthesis Reduction Cage", the specifications of which are incorporated by reference in their entireties.

This application claims priority from provisional application U.S. Ser. No. 61/466,302, filed Mar. 22, 2011, and entitled "Universal Trial for Cages", and is related to non-provisional U.S. Ser. No. 13/163,397, filed on Jun. 17, 2011 which has granted as U.S. Pat. No. 9,592,063, entitled "Universal Trial for Cages", the specifications of which are incorporated by reference in their entireties.

BACKGROUND OF THE INVENTION

Interverterbal disc space shavers are frequently utilized to prepare the intervertebral disc for interbody fusion cages. However, it is often the case that too much cortical bone is removed when decorticating the vertebral endplates. As a result, the vertebrae are undesirably weakened. Shavers are one of the many sources believed to create endplate damage due to the aggressive force during shaving, improper shaver size, access/insertion trajectory angle and/or endplate irregularities, and shape that is not congruent to the disc space.

US Patent Publication no. 2007-0233130 (Suddaby) discloses tool for preparing vertebral surfaces following a discectomy has a body and a rotary cutting tool mounted at the distal end of a lever which extends through the body. The proximal end of the lever can be squeezed toward the body to force the cutting tool against the vertebral surface facing it, while the tool is rotated by turning a crank supported on the tool body, or by a motor. The cutting tool is preferably a flexible rasp or blade which can conform to and control the convexity of the prepared surface.

U.S. Pat. No. 5,454,827 (Re. 38,335) (Aust) discloses a surgical instrument includes a handle, a first stem section having a longitudinal axis and extending from the handle, and a tissue engaging member for engaging tissue. A second stem section, connected between the first stem section and the tissue engaging member, has a portion which is bendable and supports the tissue engaging member for movement between a plurality of orientations relative to the axis and to the first stem section. The surgical instrument includes a system for bending the bendable portion of the second stem section to change the orientation of the tissue engaging member relative to the axis and to the first stem section from a first orientation to a second orientation. The bendable portion of the second stem section includes a member for enabling bending movement of the bendable portion to locate the tissue engaging member at the same angle relative to the longitudinal axis of the first stem section at more than one location along the length of the bendable portion. The marketed version of this flexible shaver claims to minimize endplate damage.

US Patent Publication Numbers 2008-0221586 and 2010-0076502 (Alphatec I and II) disclose a curvilinear access device having an expandable working portal. 2010-0076502 discloses a curved cannula (FIG. 22) having a distally extending tooth (FIG. 42); a curved stylet (FIGS. 26 and 77); a curved guidewire (FIG. 78) in a telescoping cannula (FIG. 59b); and a jointed endplate shaver (FIGS. 67a and 95).

SUMMARY OF THE INVENTION

Several devices and methods are disclosed for preparing the vertebral endplates while minimizing damage to the vertebral endplates. Each design incorporates a flexible cutting means that reduces the severity of endplate damage while enabling the removal of cartilage adhered to the cortical endplate.

Therefore, in accordance with the present invention, there is provided (Claim 1) a flexible shaver for preparing a vertebral endplate, comprising:
 a) a shaft having a proximal end portion and a distal end portion,
 b) a handle attached to the proximal end portion of the shaft, and
 c) a shaving head attached to the distal end portion of the shaft, the head comprising:
   i) a body portion;
   ii) a first face having a first recess forming a first cutting edge and
   iii) a second opposing face having a second recess forming relief groove,
 wherein the first and second recesses form a flexible cutting edge portion therebetween comprising the cutting edge.

Also in accordance with the present invention, there is provided an endplate shaver comprising:
 a) a shaft having a proximal end portion and a distal end portion,
 b) a handle attached to the proximal end portion of the shaft, and
 c) a shaving head attached to the distal end portion of the shaft, the head comprising a flexible portion, and
 wherein the head forms an angle with the shaft of at least one degree under a load of 300 N.

Preferably, the head forms an angle with the shaft of between 1 and 90 degrees under a load of 300 N. More preferably, the head forms an angle with the shaft of between 1 and 45 degrees under a load of 300 N.

Also in accordance with the present invention, there is provided (Claim 2) a flexible shaver for preparing a vertebral endplate, comprising:
a) a shaft having a proximal end portion and a distal end portion,
b) a handle attached to the proximal end portion of the shaft, and
c) a shaving head attached to the distal end portion of the shaft, the head comprising:
   i) a body portion having an upper face and a lower face;
   ii) a first row of teeth, each tooth extending from the upper face from a first respective junction;
   iii) a second row of teeth, each tooth extending from the lower face from a second respective junction;
wherein each tooth has a thickness and each respective junction has a thickness, and
wherein the thickness of at least one tooth is greater than the thickness of its respective junction to impart flexibility to the tooth.

Also in accordance with the present invention, there is provided (Claim 3) a flexible shaver for preparing a vertebral endplate, comprising:
a) a shaft having a proximal end portion and a distal end portion,
b) a handle attached to the proximal end portion of the shaft, and
c) a shaving head attached to the distal end portion of the shaft, the head comprising:
   i) a body portion having an upper portion, a lower portion, a proximal portion and a distal portion, the body portion having a first window extending between the proximal and distal portions;
   ii) a first row of teeth extending from the upper portion;
   iii) a second row of teeth extending from the lower portion,
wherein the first window imparts flexibility to the body portion.

Also in accordance with the present invention, there is provided a flexible shaver for preparing a vertebral endplate, comprising:
a) a shaft having a proximal end portion and a distal end portion,
b) a handle attached to the proximal end portion of the shaft, and
c) a shaving head attached to the distal end portion of the shaft, the head comprising:
   i) a body portion having an upper face, a lower face and a pair of side faces, the flexible body portion having a first window extending between the pair of side faces; the window forming upper and lower inner surfaces,
   ii) a first cutting surface extending from the upper face;
   iii) a second cutting surface extending from the lower face,
wherein the upper inner surface has a proximal and a distal groove therein,
wherein the lower inner surface has a proximal and a distal groove therein,
wherein each groove imparts flexibility into the shaving head.

Also in accordance with the present invention, there is provided a flexible shaver for preparing a vertebral endplate, comprising:
a) a shaft having a proximal end portion and a distal end portion,
b) a handle attached to the proximal end portion of the shaft, and
c) a shaving head attached to the distal end portion of the shaft, the head comprising:
   i) a body portion having an upper face, a lower face, a distal face and a pair of side faces, the body portion having a deep recess in the distal face extending proximally to form upper and lower extensions,
   ii) a first cutting surface extending from the upper face;
   iii) a second cutting surface extending from the lower face,
wherein the deep recess imparts flexibility to the extensions.

Also in accordance with the present invention, there is provided a flexible shaver for preparing a vertebral endplate, comprising:
a) a shaft having a proximal end portion and a distal end portion,
b) a handle attached to the proximal end portion of the shaft, and
c) a shaving head attached to the distal end portion of the shaft, the head comprising:
   i) a body portion having an upper face and a lower face,
   ii) a first cutting element spring-biased against the upper face,
   iii) a second cutting element spring-biased against the lower face.

DESCRIPTION OF THE FIGURES

FIGS. 1A-1C disclose various views of a shaver of the present invention having relief grooves that impart flexibility to the cutting edge portion.

DETAILED DESCRIPTION OF THE INVENTION

Figure 1C:
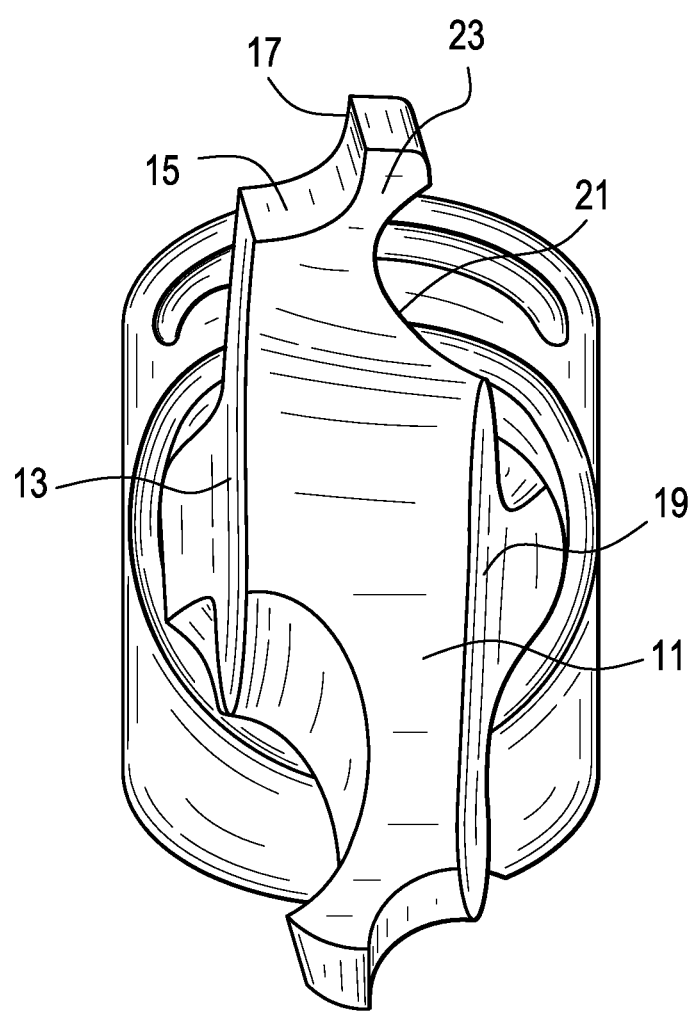
Figure 2A:
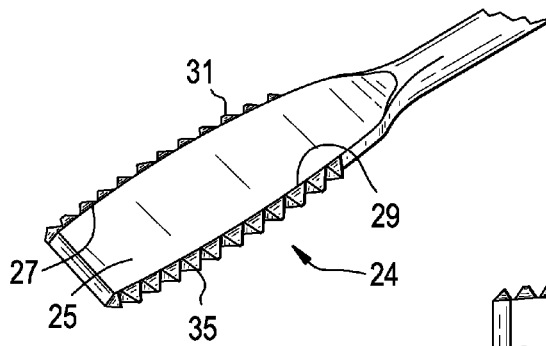
FIGS. 2A-2F disclose various views of a solid shaver having flexible teeth.
Figure 2B:
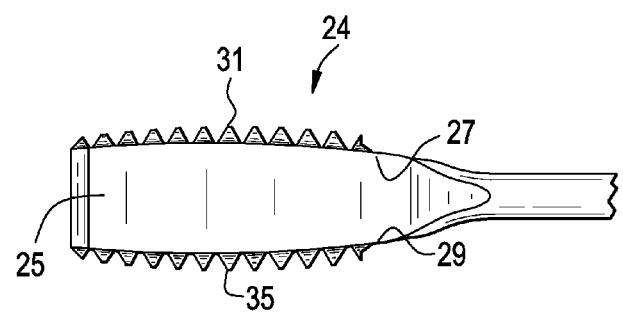
Figure 2C:
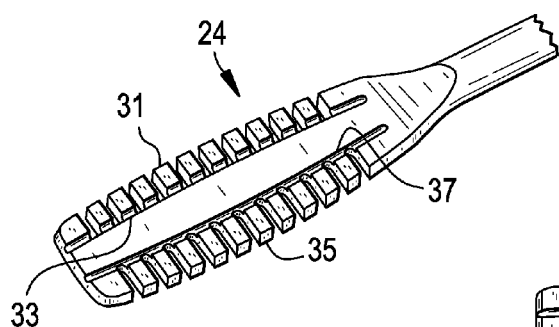
Figure 2D:
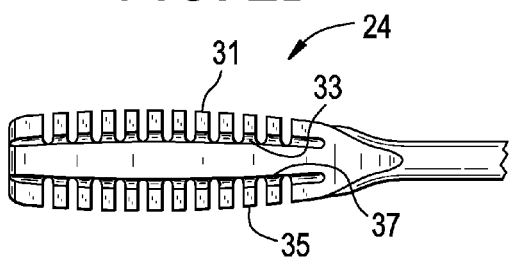
Figure 2F:
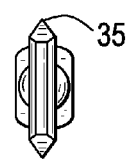
Figure 2E:
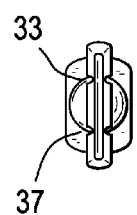
Figure 3C:
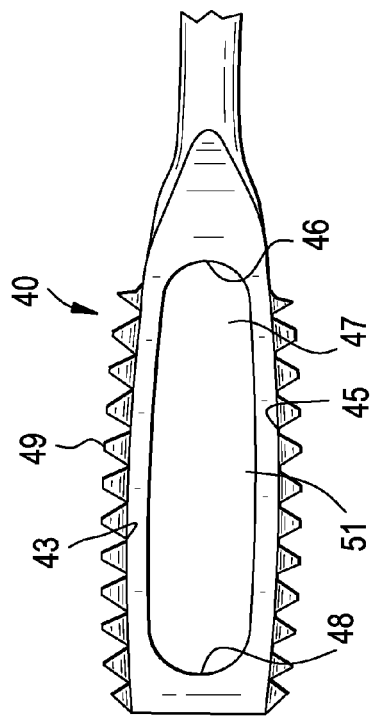
FIGS. 3A-3D disclose various views of flexible open shavers having flexibility-imparting windows.
Figure 3D:
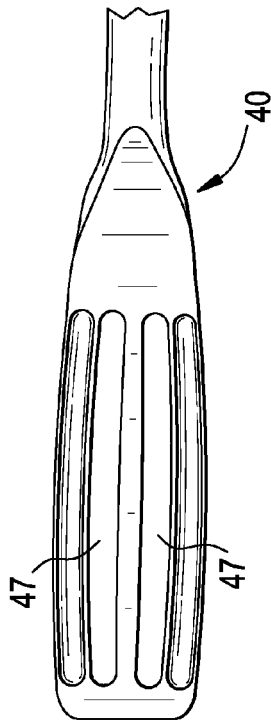
Figure 3A:
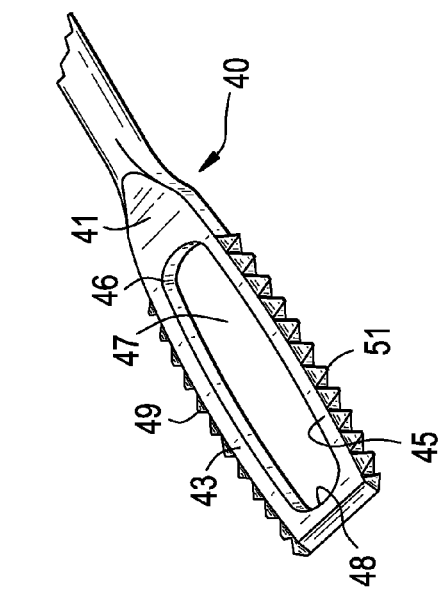
Figure 3B:
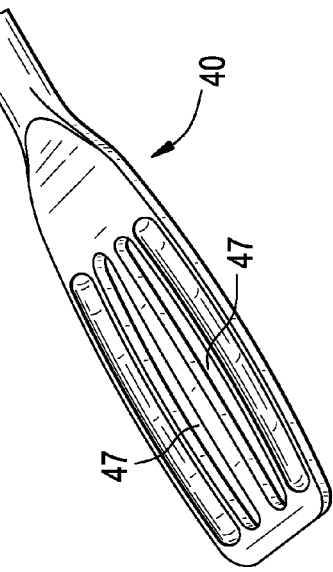

Now referring to FIGS. 1A-1C, there is provided a flexible shaver for preparing a vertebral endplate, comprising:
a) a shaft 1 having a proximal end portion 3 and a distal end portion 5,
b) a handle (not shown) attached to the proximal end portion of the shaft, and
c) a shaving head 9 attached to the distal end portion of the shaft, the head comprising:
   i) a (typically inflexible) body portion 11;
   ii) a first face 13 having a first recess 15 forming a first cutting edge 17 and
   iii) a second opposing face 19 having a second recess 21 forming a relief groove,
   wherein the first and second recesses form a flexible cutting edge portion 23 therebetween comprising the cutting edge.

The solid flexible shaver of FIGS. 1A-1C acts in a manner similar to a conventional rigid endplate shaver, except that it is designed to deflect upon excessive torque load, thereby preventing excessive endplate damage. Preferably, a non-rigid material is utilized as the material of construction for this shaver, including polyethersulfone, polyphenylsulfone, polyurethane, polyamides, polyimides, PEEK, polyethylene, polypropylene, and superelastic materials. In another embodiment, a spring steel is used to provide the flexing. The selected material and geometry of the shaver are such that the shaving head experiences only elastic deformations and easily recovers following loading. In some embodiments, features may be added to the solid flexible shaver to enable bending at specific locations to prevent endplate damage at known torsion loads and/or at a specific disc space height(s).

Now referring to FIGS. 2A-2F, there is provided a flexible shaver for preparing a vertebral endplate, comprising:
 a) a shaft having a proximal end portion and a distal end portion,
 b) a handle (not shown) attached to the proximal end portion of the shaft, and
 c) a shaving head 24 attached to the distal end portion of the shaft, the head comprising:
  i) a (typically inflexible) body portion 25 having an upper face 27 and a lower face 29;
  ii) a first row of teeth 31, each tooth extending from the upper face from a first respective junction 33;
  iii) a second row of teeth 35, each tooth extending from the lower face from a second respective junction 37;
 wherein each tooth has a thickness and each respective junction has a thickness, and
 wherein the thickness of at least one tooth is greater than the thickness of its respective junction.

In the FIGS. 2A-2F, solid shavers are disclosed with flexible teeth that independently elastically deform, thereby enabling preparation of the variable surface of the endplate while minimizing endplate damage. The size and shape of the teeth can be modified to control stiffness and relief. Bend grooves at junctions 33 and 37 ensure teeth flexibility at a known location and/or a known load.

Now referring to FIGS. 3A-3D, there is provided a flexible shaver for preparing a vertebral endplate, comprising:
 a) a shaft having a proximal end portion and a distal end portion,
 b) a handle attached to the proximal end portion of the shaft, and
 c) a shaving head 40 attached to the distal end portion of the shaft, the head comprising:
  i) a body portion 41 having an upper portion 43, a lower portion 45, a proximal portion 46 and a distal portion 48, the body portion having a first window 47 extending between the proximal and distal portions;
  ii) a first row of teeth 49 extending from the upper portion;
  iii) a second row of teeth 51 extending from the lower portion,
 wherein the first window imparts flexibility to the body portion.

The open flexible shaver of FIGS. 3A-3D, incorporates one or more open areas or internal windows in the shaving head. Upon exposure of a beam to a critical load, the window provides leaf spring-type elastic deformation of the shaver beam (such beams being formed as the upper, lower, proximal and distal portions around the window) that flex inward. A relatively non-rigid material of construction may be utilized including polyethersulfone, polyphenylsulfone, polyurethane, polyamides, polyimides, PEEK, polyethylene, polypropylene, and superelastic materials. In other embodiments, spring steel is used. The windows also provide a means for disc tissue removal as tissue is collected in the windows following shaving.

Figure 4A:
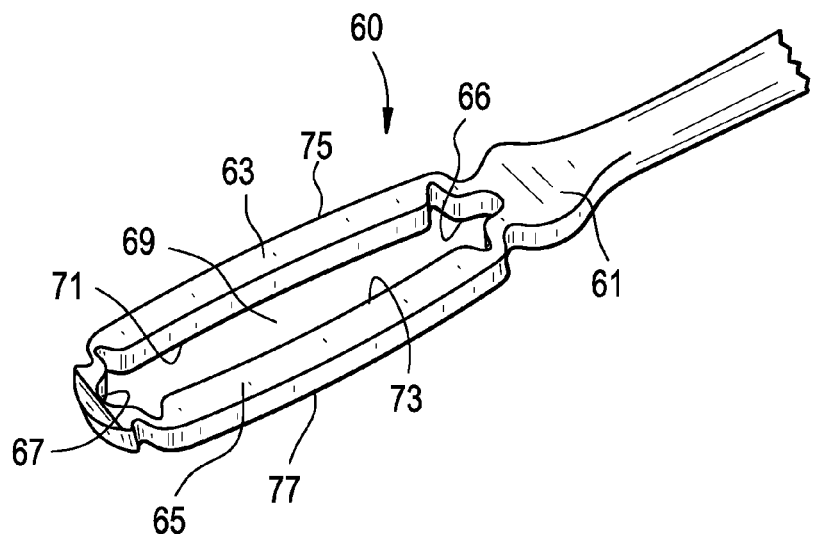
FIGS. 4A-4B disclose various views of flexible open shavers having a flexibility-imparting window having grooves in its corners.
Figure 4B:
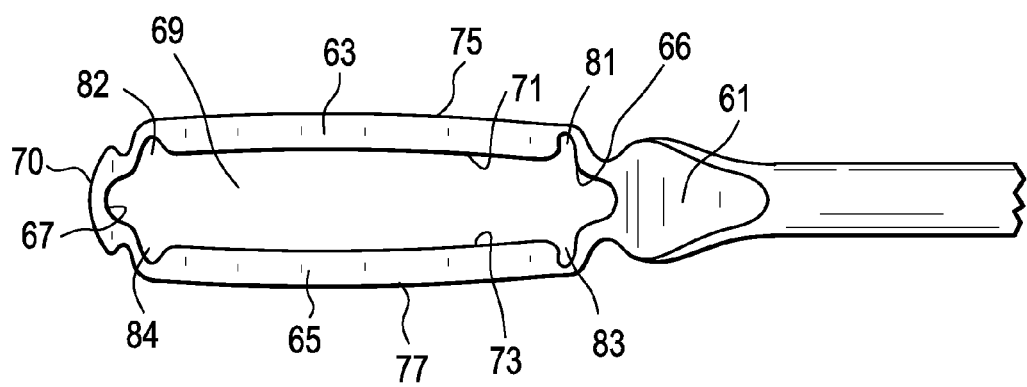

Now referring to FIGS. 4A-4B, there is provided a flexible shaver for preparing a vertebral endplate, comprising:
 a) a shaft having a proximal end portion and a distal end portion,
 b) a handle attached to the proximal end portion of the shaft, and
 c) a shaving head 60 attached to the distal end portion of the shaft, the head comprising:
  i) a body portion 61 having an upper portion 63, a lower portion 65, a proximal portion 66 and a distal portion 67, the flexible body portion having a first window 69 extending between the proximal and distal portions; the window forming upper 71 and lower 73 inner surfaces,
  ii) a first cutting surface 75 extending from the upper portion;
  iii) a second cutting surface 77 extending from the lower portion,
 wherein the upper inner surface has a proximal 81 and a distal 82 groove therein,
 wherein the lower inner surface has a proximal 83 and a distal 84 groove therein,
 wherein each groove imparts flexibility into the shaving head.

The open shaver of FIGS. 4A-4B incorporates a plurality of flexion grooves that provide elastic deformation at known loads and/or locations. For example, the grooves can be spaced/sized in order to provide variable flexibility at specific locations.

In other embodiments, the inner surfaces have more than two grooves. As shown in FIG. 4B, the distal end of the shaver can have a bulleted nose 70.

Figure 5A:
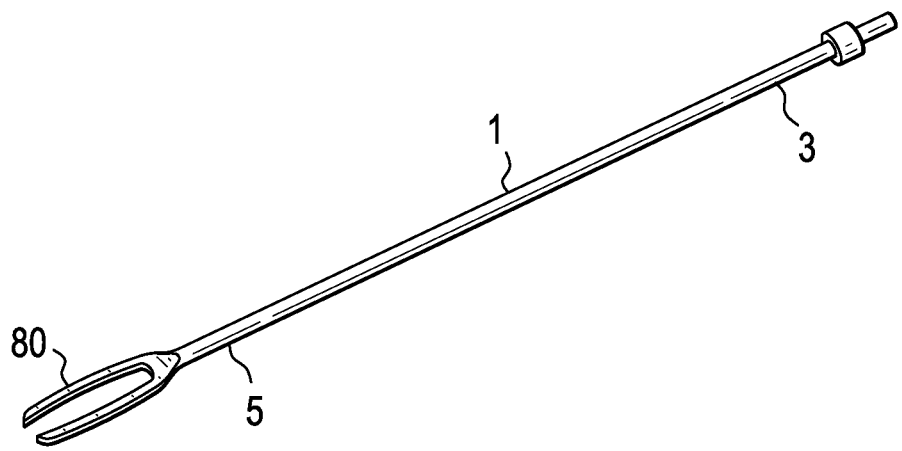
FIGS. 5A-5B disclose various views of a forked shaver.
Figure 5B:
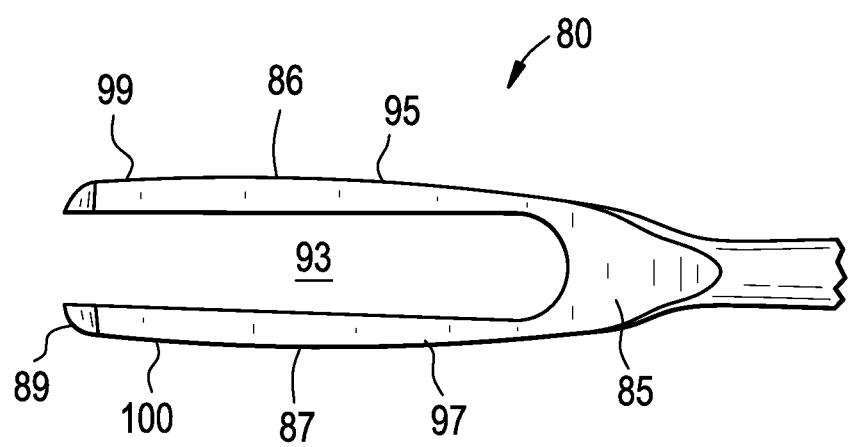

Now referring to FIGS. 5A-5B, there is provided a flexible shaver for preparing a vertebral endplate, comprising:
 a) a shaft 1 having a proximal end portion 3 and a distal end portion 5,
 b) a handle (not shown) attached to the proximal end portion of the shaft, and
 c) a shaving head 80 attached to the distal end portion of the shaft, the head comprising:
  i) a body portion 85 having an upper face 86, a lower face 87, and a distal face 89, the body portion having a deep recess 93 in the distal face extending proximally to form upper 95 and lower 97 extensions,
  ii) a first cutting surface 99 extending from the upper face;
  iii) a second cutting surface 100 extending from the lower face,
 wherein the deep recess imparts flexibility to the extensions.

The open shaver of FIGS. 5A-5B can be "forked" to control the amount of deflection and associated endplate preparation force applied to contra-lateral, anterior, or posterior aspects of the disc space. The extensions of the fork can be parallel, diverging or converging.

Figure 6A:
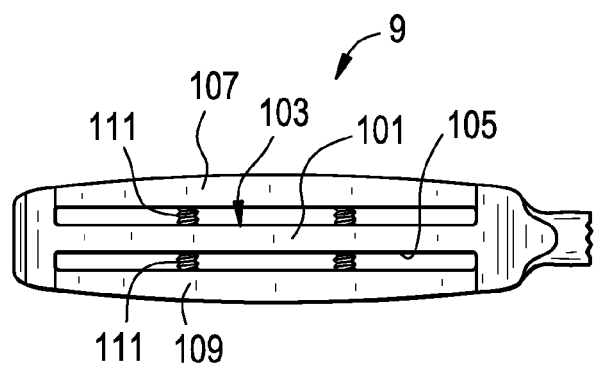
FIGS. 6A-6E disclose various views of spring-biased shavers.
Figure 6B:
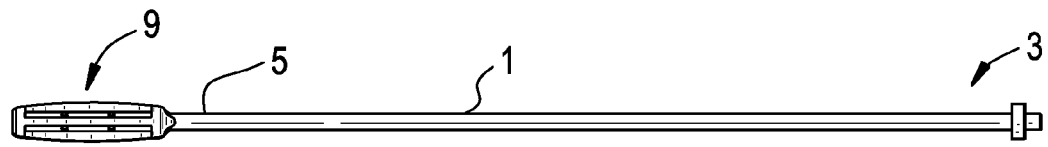

Now referring to FIGS. 6A-6B, there is provided a flexible shaver for preparing a vertebral endplate, comprising:
 a) a shaft 1 having a proximal end portion 3 and a distal end portion 5,
 b) a handle attached to the proximal end portion of the shaft, and
 c) a shaving head 9 attached to the distal end portion of the shaft, the head comprising:
  i) a body portion 101 having an upper face 103 and a lower face 105, ii) a first cutting element 107 spring-biased against the upper face, iii) a second cutting element 109 spring-biased against the lower face.

This spring shaver incorporates one or more inner compression springs 111 including a coil, a belleville washer, a leaf spring, and an elastic bumper. These springs support the floating cutting blades of the shaver. When the springs experience an excessive load, the springs compress and cause the shaver blades to retract, thereby reducing the amount of endplate damage. The shaver blade and associated springs can be segregated to control amount of deflection and associated endplate preparation force applied to contra-lateral, anterior, or posterior aspects of the disc space. Either the shaver blade geometry or the amount of spring force incorporated for the segregated blades can be modified to provide lordosis during endplate preparation.

Figure 6C:
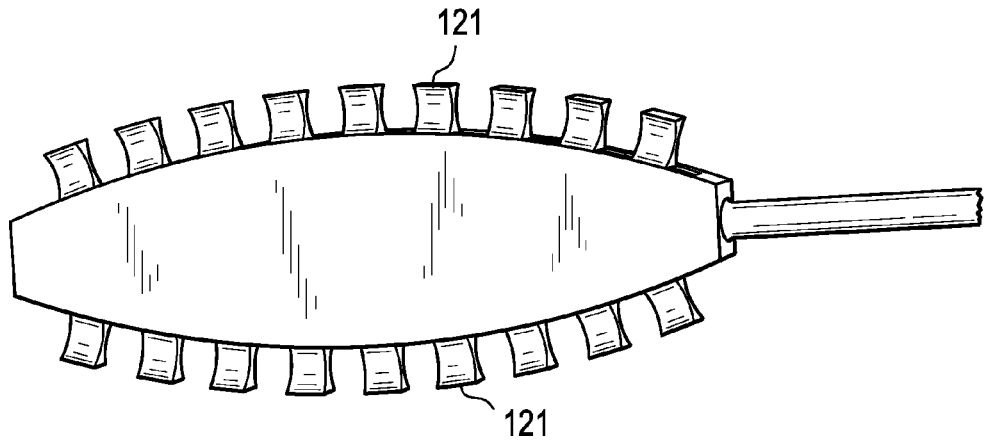
Figure 6D:
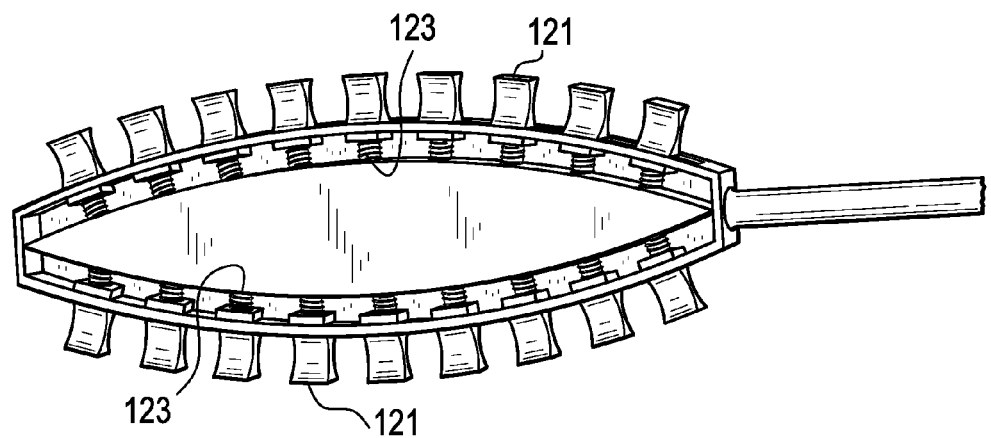
Figure 6E:
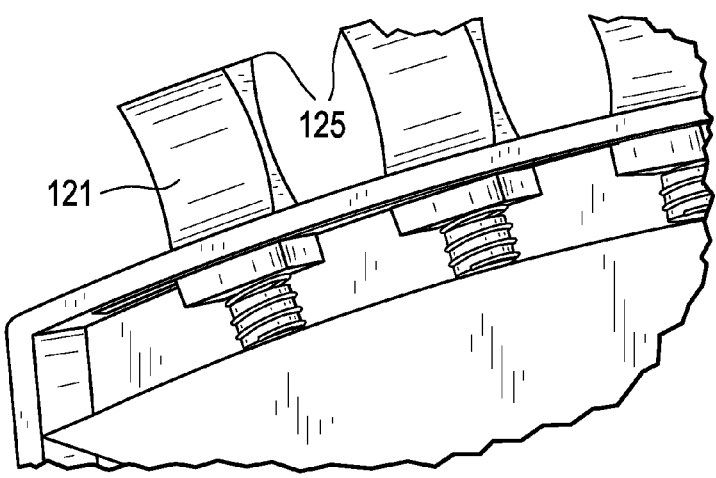

Now referring to FIGS. 6C-6E, there is provided an embodiment having individually spring-loaded teeth. The teeth 121 are arranged in a curved contour to better adhere to anatomical configurations. There can be a different number of teeth based on user preference or optimization activities. These teeth recess into the body of the shaver in response to shaver-bone contact and they are pushed back out to their initial position by axial springs 123 when the contact is removed. The teeth have cutting surfaces 125 that are designed to shave intrer-discal tissue when the instrument is being rotated in the clockwise or counterclockwise direction. However, the teeth could be designed for unidirectional cutting if desired. The advantage of this design is such that if and when the individual cutting teeth accidentally hit bone formations or contours, they are able to recess without damaging the bone but are still able to cut and remove soft tissue. The extent to which these teeth are able to move in and out of the shaver head can be tuned in through spring selection. It is believed that this embodiment may provide a more anatomically-responsive shaver in any part of the disc space through its shape adaptations. Overall, this instrument will help prevent endplate damage and will allow for proper cage placement without the incidence of gross subsidence.

In using the shaver, the surgeon will typically precut the disc annulus to create an entry window. The surgeon then inserts the distal end of the shaver into the disc space. The top and bottom faces are preferably parallel to the endplates upon insertion. The surgeon then rotates the shaver to rotate the cutting edges against the vertebral endplates. As the shaver with cutting edges is rotated, the disc nucleus pulposus, annulus, and cartilaginous tissue are cut or excised from the vertebral endplates. The shaver flexibility allows for deflection at locations where excessive loads are being incurred, thereby preventing excessive endplate damage. The shaver can be advanced further into the disc such that the contra-lateral aspects of the disc including the annulus are cut and excised. Following use, the shaver is withdrawn from the disc and any tissue which has accumulated within the shaver windows is removed. Shavers from a kit of various sizes, geometries or flexibilities can be used to customize the disc clearing and control the amount of cartilaginous tissue from the endplate.

The surgeon can perform the surgery with the flexible shavers from the any access location of the disc including posterior, lateral, anterior-lateral or lateral.

In certain embodiments, these flexible shavers are used to prepare vertebral endplates associated with the L5/S1 functional spinal unit for the lateral insertion of a fusion cage.

Therefore, in accordance with the present invention, there is provided a method of preparing a vertebral endplate, comprising the steps of:

a) removing an intervertebral disc to create a disc space and expose first and second vertebral endplates, b) inserting a shaver of the present invention into the disc space, and c) moving the shaver against at least one of the vertebral endplates to remove cartilage from the vertebral endplate.

In preferred embodiments, the method comprises the steps of:

i) selecting an endplate shaver comprising:
  a. a shaft having a proximal end portion and a distal end portion,
  b. a handle attached to the proximal end portion of the shaft, and
  c. a shaving head attached to the distal end portion of the shaft, the head comprising a flexible portion, and ii) contacting the shaving head to the vertebral body endplate to shave the endplate.

When a flexible material is selected as the material of construction for a shaver of the present invention, the flexible material is preferably selected from the group consisting of polyethersulfone, polyphenylsulfone, polyurethane, polyamides, polyimides, PEEK, polyethylene, polypropylene, and superelastic materials. When a rigid material is selected as the material of construction for a shaver of the present invention, the rigid material is preferably a metal and is more preferably selected from the group consisting of stainless steel, chromium cobalt, and titanium alloy.

In some embodiments, there is provided a kit of a plurality of shavers of the present invention. The shavers in the kit may be of different sizes, or of different flexibilities, or both. Some kits of the present invention may include a plurality of identical shavers. Some kits may include a standard shaft-and-handle component to which may be attached a plurality of modular shaving heads.

In some embodiments, there is provided an assembly comprising:

a) a curved port having a bore having a transverse cross-section; and b) a vertebral endplate shaver having a transverse cross-section, wherein the shaver is disposed within the bore of the curved port, wherein the transverse cross-section of the bore substantially corresponds to the transverse cross-section of the shaver so as to determine the orientation of the shaver within the bore.

We claim:

1. An assembly comprising:

a port having a bore having a transverse cross-section; and a vertebral endplate shaver having a transverse cross-section, wherein the shaver is disposed within the bore of the port and comprises:

a) a shaft having a proximal end portion and a distal end portion, b) a handle attached to the proximal end portion of the shaft, and c) a shaving head attached to the distal end portion of the shaft, the head comprising:

i) a body portion having an upper portion, a lower portion, a proximal body portion and a distal body portion, the body portion having a first window extending longitudinally between the proximal and distal body portions, and between its upper portion and lower portion;

wherein the proximal body portion connects the upper and lower portions of the body;

wherein the proximal body portion attaches to the distal end portion of the shaft, wherein the first window imparts flexibility to the body portion and provides leaf spring-type elastic deformation of the shaving head under a load perpendicular to the upper and lower portions, wherein the upper portion and lower portion of the body portion, the proximal body portion and the distal body portion are monolithic, wherein the distal body portion connects the upper portion to the lower portion.

2. The assembly of claim 1 wherein the head further comprises:
ii) a first row of teeth extending from the upper portion;
iii) a second row of teeth extending from the lower portion.

3. The assembly of claim 1 wherein the flexible body portion further comprises a second window extending between the proximal and distal portions of the body portion.

* * * * *